United States Patent [19]

Williams et al.

[11] Patent Number: 4,467,065

[45] Date of Patent: Aug. 21, 1984

[54] SEMI-CRYSTALLINE POLYMERS STABILIZED FOR IRRADIATION STERILIZATION

[75] Inventors: Joel Williams, Cary; Terry Dunn; Vivian Stannett, both of Raleigh, all of N.C.

[73] Assignee: Becton Dickinson and Company, Paramus, N.J.

[21] Appl. No.: 223,526

[22] Filed: Jan. 8, 1981

Related U.S. Application Data

[62] Division of Ser. No. 74,250, Sep. 10, 1979, Pat. No. 4,274,932.

[51] Int. Cl.$^3$ .......................... C08K 5/00; C08K 5/01; C08K 5/02; C08K 5/12
[52] U.S. Cl. .................................. 524/296; 604/199; 204/159.14; 204/159.18; 204/159.2; 250/429; 422/22; 523/300; 524/78; 524/261; 524/583; 524/585; 524/587

[58] Field of Search ................ 260/31.8 PQ, 33.6 PQ, 260/29.1 SB, 23 H, 33.8 UA; 523/300; 524/78, 261, 296, 583, 585, 587

[56] References Cited

U.S. PATENT DOCUMENTS

| | | | |
|---|---|---|---|
| 3,201,364 | 8/1965 | Salyer | 260/33.6 PQ |
| 3,496,124 | 2/1970 | Needham et al. | 260/33.6 PQ |
| 3,537,967 | 11/1970 | Kelley et al. | 204/159.18 |
| 3,940,325 | 2/1976 | Hirao | 204/159.2 |
| 4,110,185 | 8/1978 | Williams et al. | 204/159.2 |
| 4,259,468 | 3/1981 | Kajiura et al. | 526/283 |

Primary Examiner—Stanford M. Levin

[57] ABSTRACT

Semi-crystalline polymer having a narrow molecular weight distribution and having incorporated therein a non-crystalline mobilizing additive which increases the free volume of the polymer, with such a combination preventing embrittlement of the polymer during and subsequent to irradiation sterilization.

11 Claims, 3 Drawing Figures

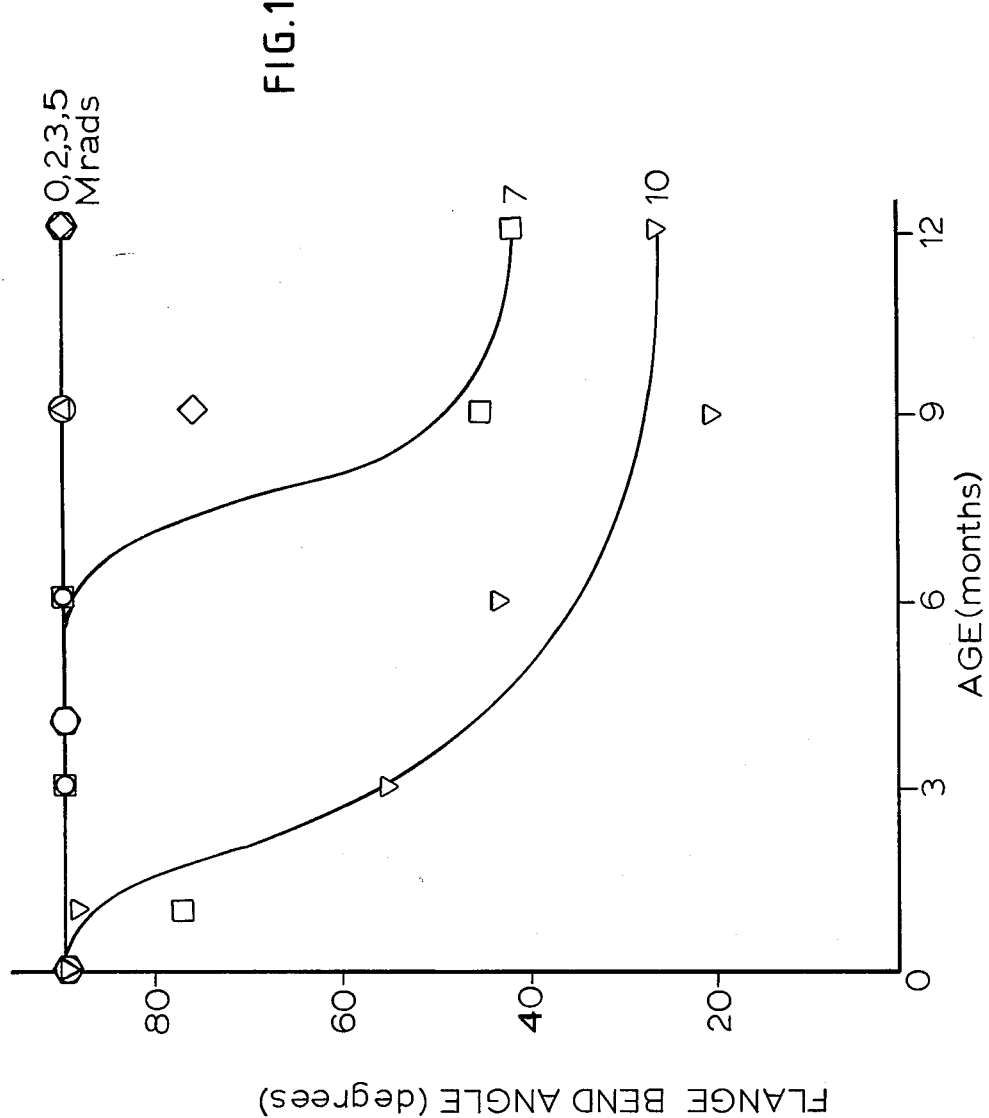

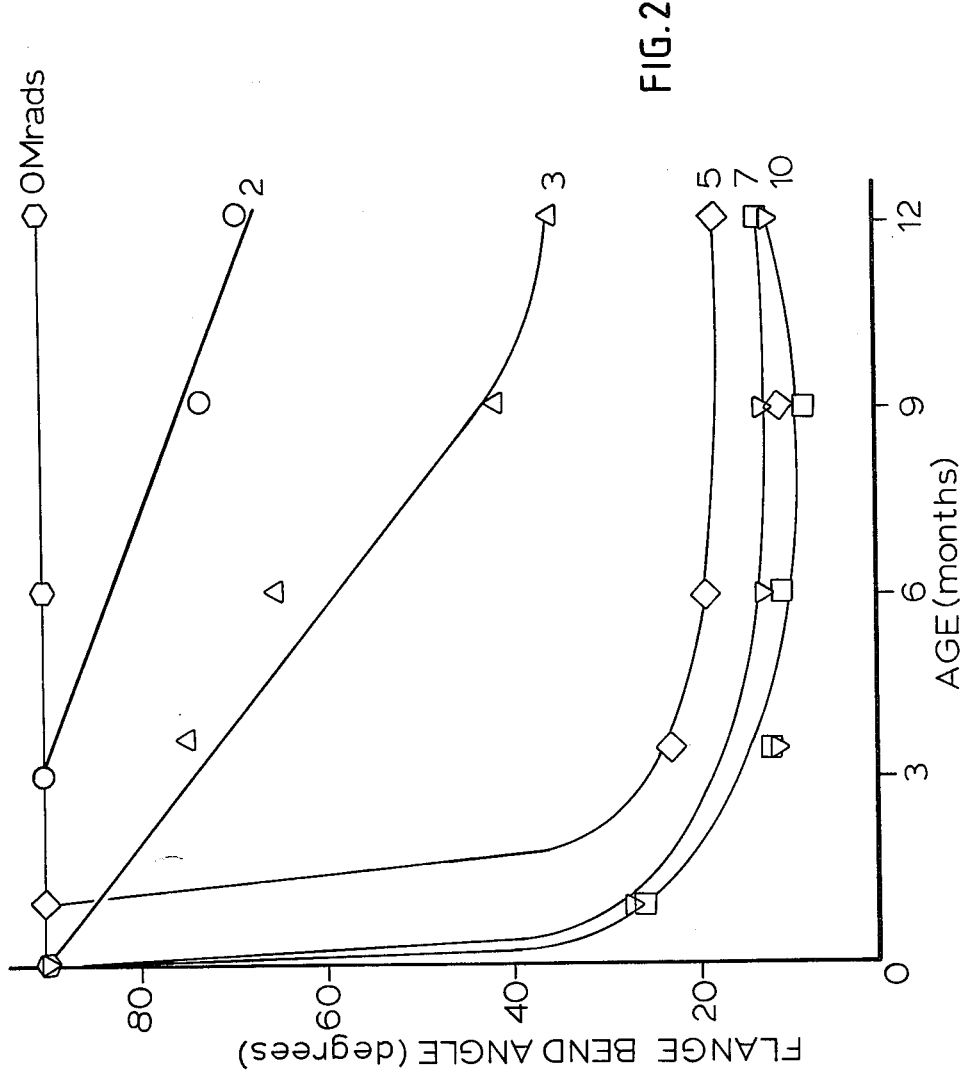

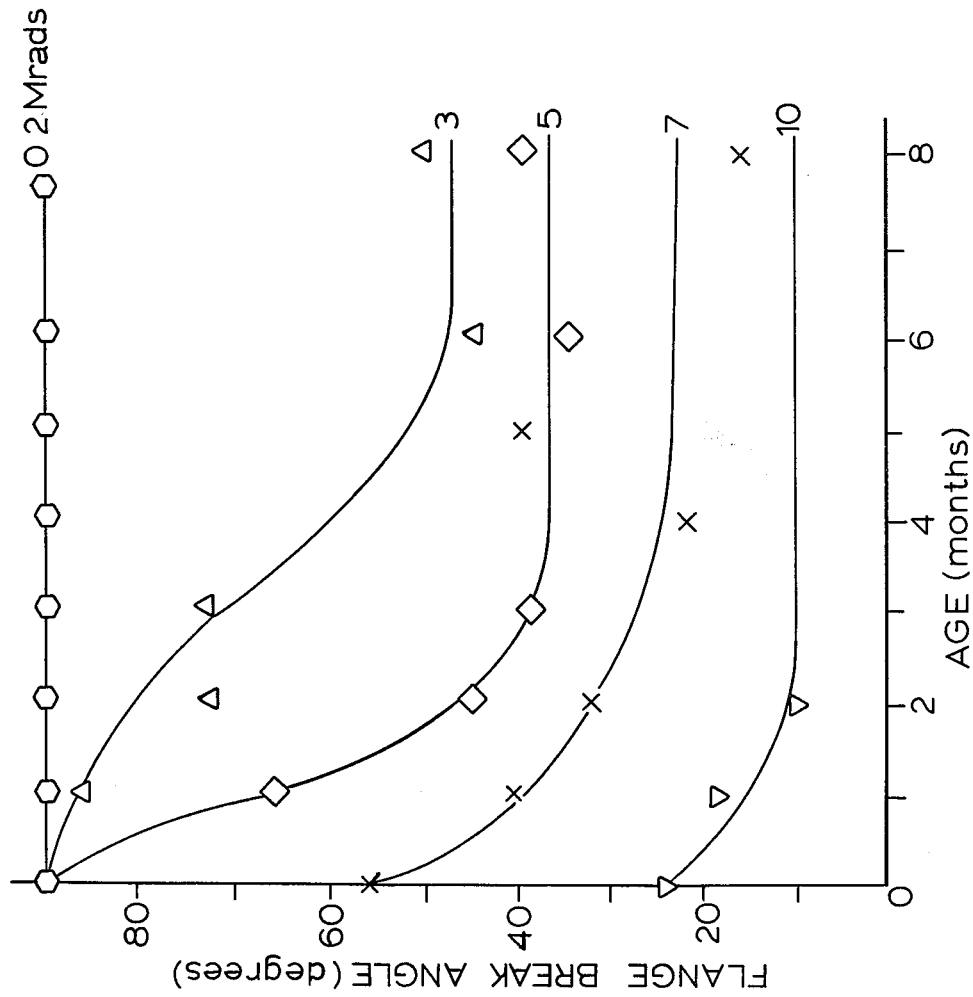

SEMI-CRYSTALLINE POLYMERS STABILIZED FOR IRRADIATION STERILIZATION

This is a division of application Ser. No. 74,250, filed Sept. 10, 1979, now U.S. Pat. No. 4,274,932.

This invention relates to semi-crystalline polymers which are stabilized for irradiation sterilization.

Semi-crystalline polymeric materials, such as polypropylene, are often employed in articles where it is necessary to subject the article to irradiation sterilization. Such materials, however, degrade during or subsequent to such irradiation; i.e., during shelf storage time, and as a result of such degradation, the articles become embrittled.

U.S. Pat. No. 4,110,185 discloses irradiation sterilization of semi-crystalline polymers wherein the semi-crystalline polymer has incorporated therein a non-crystalline mobilizing additive which increases the free volume of the polymer to thereby prevent embrittlement of the polymer during and subsequent to the irradiation.

The present invention is directed to an improvement in the irradiation stabilization of a semi-crystalline polymer.

In accordance with one aspect of the present invention, there is provided a semi-crystalline polymer, which has a narrow molecular weight distribution, and which has incorporated therein a mobilizing amount of a non-crystalline mobilizer. Applicant has found that the combination of a mobilizing additive and a narrow molecular weight distribution provides improvement in the irradiation stability of such polymers. Accordingly, such semi-crystalline polymer having a mobilizing additive incorporated therein even subjected to sterilizing irradiation, has an increased stability to embrittlement during and subsequent to such irradiation.

The molecular weight distribution of a polymer is defined by the ratio of the weight average molecular weight to the number average molecular weight. In accordance with the present invention, such ratio should not be greater than 9.0, preferably no greater than 8.0 and most preferably no greater than 6.0. The minimum ratio, by definition is 1.0. As a practical matter the ratio is at least 2.0 in that polymer production costs are increased in the production of polymers having a ratio in the order of from 1.0 to 2.0. In most cases, the ratio is in the order of from 2.0 to 4.0.

The mobilizer is a low molecular weight non-crystalline substance, which is miscible with the polymeric material and is also compatible therewith; i.e., the mobilizer does not adversely affect the properties of the polymer. The mobilizer is a substance which increases the free volume of the polymer and, therefore, also lowers the density of the polymer. The mobilizer functions to mobilize the amorphous portion of the polymer, and as a result, increases the radical termination reactions which prevent or minimize degradation during and subsequent to the irradiation.

The mobilizer can be any one of a wide variety of liquids which increase the total free volume of the polymer. The term liquid as used herein includes highly viscous substances, commonly referred to as greases. In general, such mobilizers have a density of from 0.6 to 1.9 g/cm$^3$, and preferably of from 0.6 to 1.1 g/cm$^3$. The mobilizer has a low molecular weight, with the average molecular weight, generally being in the order of from 100 to 10,000 grams/mole, and preferably from 100 to 5,000 grams/mole.

As representative examples of suitable mobilizers, there may be mentioned: hydrocarbon oils, halogenated hydrocarbon oils, phthalic ester oils, vegetable oils, silicone oils, low molecular weight non-crystalline polymer greases, such as hydrocarbon polymer greases, low molecular weight polyester greases, polyarylether greases, etc. It is to be understood that the above examples are only illustrative and the use of other mobilizers should be apparent to those skilled in the art from the teachings herein. The preferred mobilizer is a liquid mobilizer which is not highly viscous, and in particular, a hydrocarbon oil or phthalic ester oil.

The polymers employed in the present invention are semi-crystalline polymers, with such polymers having a crystalline content on the order of from 20 to 90%, and preferably of from 40% to 80%. The polymer may be comprised of one, two or more monomers, and the term polymer generically refers to both homopolymers and copolymers comprised of two or more monomers. As representative examples of suitable polymers, there may be mentioned: polymers of propylene, ethylene, oxymethylene, butylene, etc. The preferred polymer is polypropylene.

The mobilizer is incorporated into the polymer in a mobilizing amount, with such mobilizer generally being present in an amount of from 0.01% to 50% and preferably of from 0.1% to 20%, all by weight.

The polymer may also include other additives which are conventionally used in the art, such as antioxidants, preservatives, fillers, etc.

The polymer of narrow molecular weight distribution, preferably polypropylene, including the liquid mobilizer can be employed to produce an article which is to be sterilized by procedures known in the art. As representative examples of such articles, there may be mentioned: syringes, tube assemblies, tissue culture flasks, needles, package film, etc.

The polymer of narrow molecular weight distribution having the mobilizer incorporated therein, either as the polymeric material per se, or as an article, e.g., a syringe or package film, can be sterilized by subjecting the polymer to a sterilizing of high energy radiation. The high energy radiation can be provided by any one of a variety of sources, including cobalt 60, high energy electrons and X-rays. In general, the sterilizing radiation doses are on the order of from 0.5 to 5.0 megarads, with the typical dose being 1.0 to 3.5 megarads. It is to be understood that higher doses could be employed, but are generally not necessary.

It has been found that by effecting the radiation sterilization of a semi-crystalline polymer of narrow molecular weight distribution having incorporated therein a mobilizer, the sterilized or irradiated polymer is not embrittled, and moreover, does not become embrittled subsequent to the irradiation (no embrittlement with age); i.e., the polymer retains its flexibility. Thus, for example, prior to irradiation, such polymers have a bending angle of at least 90°, and in accordance with the present invention, the irradiated polymer subsequent to irradiation and even after storage for a long period of time has a bending angle of at least 90°.

The invention will be further described with respect to the following examples; however, the scope of the invention is not to be limited thereby.

EXAMPLE

A narrow molecular weight distribution polypropylene, having a ratio of weight average molecular weight to number average molecular weight ($\bar{M}w/\bar{M}n$) of 2.8, containing 4.7% of a mobilizing additive (hydrocarbon oil) was irradiated to 2, 3, 5, 7, and 10 megarads. Immediately following irradiation the sample was still flexible even after 7 megarads as shown in FIG. 1. In fact, the 7.0 megarad sample remains flexible even after six months aging as shown in FIG. 1. Furthermore the 5 megarad sample remains flexible even after one year of aging. For comparison, such polypropylene containing no mobilizing additive was shown to break at even 2 megarads as summarized in FIG. 2 after only three months aging.

In addition, a broad molecular weight distribution polyproplene, $\bar{M}w/\bar{M}n=10$, containing 4.7% of the same mobilizing additive could not withstand but 2.0 megarads as shown in FIG. 3 before embrittlement.

Thus, the combination of a narrow molecular weight distribution with a mobilizing additive provides a significant improvement as to resistance to embrittlement during and subsequent to irradiation, as compared to a polymer of broad molecular weight distribution, which includes a mobilizing additive.

In particular, at dosages above 2.0 megarads, the narrow molecular weight distribution polymer, including mobilizing additive has increased resistance to embrittlement, as compared to a broad molecular weight distribution polymer which includes a mobilizing additive. Thus, the present invention provides for the ability to use a wider range of sterilization dosages, without degradation of polymer properties.

Numerous modification and variations of the present invention are possible in light of the above teachings and, therefore, within the scope of the appended claims, the invention may be practiced otherwise than as particularly described.

We claim:

1. A composition having improved irradiation sterilization stability when subject to irradiation, comprising: A semi-crystalline polyolefin having a crystalline content of from 20–90%, and a narrow molecular weight distribution wherein the ratio of the weight average molecular weight to the number average molecular weight is no greater than 9.0 said polyolefin having incorporated therein a mobilizing amount of a non-crystalline liquid mobilizing additive which increases the free volume of the polymer, said composition resisting embrittlement during and subsequent to irradiation sterilization.

2. The composition of claim 1 wherein the said ratio is no greater than 8.0.

3. The composition of claim 1 wherein the ratio is no greater than 6.0.

4. The composition of claim 3 wherein the mobilizing additive is miscible with the polyolefin and has a molecular weight of from 100 to 10,000 grams per mole.

5. The composition of claim 4 wherein the mobilizing additive has a density of from 0.6 to 1.9 grams/cm$^3$.

6. The composition of claim 5 wherein the mobilizer is a hydrocarbon oil.

7. The composition of claim 5 wherein the mobilizing additive is a phthalic ester.

8. The composition of claim 6 wherein the polyolefin is polypropylene.

9. The composition of claim 1 wherein the polyolefin is polypropylene.

10. The composition of claim 9 wherein the ratio is from 2.0 to 4.0.

11. The composition of claim 10 wherein the mobilizing additive is a hydrocarbon oil.

* * * * *